United States Patent
Axen et al.

(10) Patent No.: US 7,074,223 B2
(45) Date of Patent: Jul. 11, 2006

(54) COATING METHOD AND COATED DEVICES

(75) Inventors: Niklas Axen, Jarlasa (SE); Leif Hermansson, Uppsala (SE); Erik Johansson, Uppsala (SE); Tobias Persson, Uppsala (SE)

(73) Assignee: CerBio Tech AB, Uppsala (SE)

( * ) Notice: Subject to any disclaimer, the term of this patent is extended or adjusted under 35 U.S.C. 154(b) by 381 days.

(21) Appl. No.: 10/322,569

(22) Filed: Dec. 19, 2002

(65) Prior Publication Data

US 2004/0247903 A1 Dec. 9, 2004

(30) Foreign Application Priority Data

Dec. 27, 2001 (SE) .................................... 0104440

(51) Int. Cl.
*A61B 17/00* (2006.01)
*B05D 1/12* (2006.01)

(52) U.S. Cl. ........................ 606/76; 428/469; 428/701; 428/702; 427/180

(58) Field of Classification Search ............ 606/76–78; 427/2.1
See application file for complete search history.

(56) References Cited

U.S. PATENT DOCUMENTS 5,269,845 A * 12/1993 Grunau et al. .............. 106/692
5,466,280 A * 11/1995 Lee et al. ................ 106/14.12

FOREIGN PATENT DOCUMENTS

| SE | 01 04441-1 | 12/2001 |
| WO | 90/11066 | 10/1990 |
| WO | 90/11979 | 10/1990 |
| WO | 00/19965 | 4/2000 |

OTHER PUBLICATIONS

S.F. Hulbert et al., "Potential of Ceramic Materials as Permanently Implantable Skeletal Prostheses," J. Biomed. Mater. Res., V. 4, 1970, pp. 433-456.

* cited by examiner

Primary Examiner—Eduardo C. Robert
Assistant Examiner—David Comstock
(74) Attorney, Agent, or Firm—Young & Thompson

(57) ABSTRACT

Surface coating method for deposition of a chemically bonded ceramic coating on a substrate, includes the steps of preparing a curable coating slurry, depositing a coating of the slurry on at least a section of the substrate surface, and hardening the slurry. The step of preparing a curable coating slurry includes mixing calcium aluminate powder with water and at least one water-reducing-agent, such that a water-to-cement ratio in the range of 0.1 to 0.9 is achieved.

22 Claims, 3 Drawing Sheets

COATING METHOD AND COATED DEVICES

THE FIELD OF THE INVENTION

The present invention relates to a method for deposition of ceramic coatings, a biocompatible surface coating and devices coated with said biocompatible surface coating, and in particular to a method for deposition of ceramic coatings having a high degree of biocompatibility and medical devices for implantation, comprising a substrate that is coated with such a biocompatible ceramic layer.

BACKGROUND OF THE INVENTION

Surface Coating Techniques

A vast variety of materials can be deposited as thin films or coatings. This invention particularly focuses on ceramic coatings. Ceramic coatings are often used for properties like, hardness, friction, corrosion resistance, and biocompatibility.

The most established techniques for depositing ceramic of coatings are CVD (Chemical Vapor Deposition), PVD (Physical Vapor Deposition), electrolytic deposition, and thermal spray deposition. Furthermore, there are numerous subgroups within each deposition technique.

CVD is a high temperature process (typically 800° C.–1000° C.), wherein a chemical reaction occurring between the surface of a substrate and a gas that is flooded over the surface, generates a surface film on the substrate. The technique is mainly used for deposition of metal carbides, -nitrides or -oxides upon temperature resistant substrates, such as hard metal. The thickness of the deposited films may be in the range from nanometers to micrometers.

PVD is based on physical processes, most often plasma techniques, and may be used at lower temperatures than CVD, typically 300° C.–500° C. at the substrate surface. Contrary to CVD, PVD processes are line of sight processes, which imply that it is not possible to deposit films around corners, inside tubes, etc. PVD may be used for deposition of pure metals and a large number of chemical compounds. PVD methods are commonly used for deposition on temperature sensitive substrates, such as steels, aluminum and even plastic materials. The coating thicknesses are of the same order of magnitude as for CVD processes.

Thermal spray deposition includes techniques based on gas flame, electric arc and gas plasma, all of which involve extremely high temperatures. The melting zone may reach temperatures in the order of 10 000° C. This set requirements on the temperature properties of both substrate and coating materials. Thermal spraying may be used for deposition of a number of metallic and ceramic materials. In general, the deposited films are thicker than for PVD and CVD, in the range of 100 micrometers to a few millimeters.

A disadvantage with existing techniques for deposition of ceramic films is the elevated temperatures required in the process. Therefore, the most preferred of the above methods is often PVD, which may be used for deposition around 300° C. Another disadvantage is that said methods require advanced deposition equipment, especially CVD and PVD, for which gas-tight vacuum-arrangements are needed.

The main disadvantage with thermal spray deposition is the temperatures of the melting zone. Also the cooling rate of the deposited material is extremely high. Cooling from typically 10 000° C. to room temperature in a few microseconds, implies that possibilities to control the microstructure of the coating are very limited. Phase-composition, chemical composition, porosity and surface structure cannot be accurately regulated.

Biocompatible Materials

As for bioceramics, hydroxyapatites, or other calcium phosphates, are of particular interest. Hydroxyapatite is osseo-compatible, since bone tissue regenerates excellently against this ceramic. The material seems to be capable of forming a direct bond with natural bone. One reason for this may be that human bone tissue is composed of about ⅔ of hydroxyapatite.

As pure bulk material hydroxyapatites and other calcium phosphates have poor mechanical properties. Hydroxyapatite is therefore often used as a coating material on metal substrates or as an additive in a stronger matrix (see WO/11979). Polymer based bone cements with hydroxy apatite fillers is an established product. However, all techniques involving elevated temperatures tend to alter the microstructure of the hydroxyapatite, e.g. that the hydration water in the hydroxyapatites leaves the structure.

Orthopedic components with hydroxyapatite based coatings deposited with various thermal spraying techniques, form a relatively large group of implants. Attempts have also been made to produce bio (or osseo-) compatible coatings of coral-like materials of calcium carbonates. However, the limited mechanical properties of these materials set limitations to their use.

Calcium Aluminates

Another bioceramic is calcium aluminate, and its medical applications is described e.g. in S. F. Hulbert, F. A. Young, R. S. Mathews, J. J. Klawitter, C. D. Talbert. It is shown that tissues (bone, muscular, subcutaneous fat) to a large extent do not react when put in contact with pure calcium aluminate, i.e. no irritation, inflammations, or toxic reactions occur.

SE-463 493 discloses a chemically bound ceramic material comprising aluminates and silicates. The material is achieved through a production technique involving pre-compaction of the ceramic body. In addition, the ceramic material may comprise an inert phase of e.g. hydroxyapatite or oxides of titanium, zirconium, zinc and aluminium.

Calcium aluminate has been explored as a tooth filling material, e.g. the product Doxadent® produced by Doxa Certex AB, see e.g. PCT/SE99/01729, "Sätt att framställa en kemiskt bunden keramisk produkt, samt produkt", 29, Sep. 1999.

SUMMARY OF THE INVENTION

The object of the invention is to provide a new method for deposition of a chemically bonded ceramic surface coating, a biocompatible surface coating and a surface coated device, such that the drawbacks of the prior art are overcome. This is achieved by the method as defined in claim 1.

One advantage with the method is that it is a low temperature process, it can be used to deposit ceramic coatings on temperature sensitive substrates.

Another advantage is that the coated device has improved biocompatibility, particularly in contact with bone.

Still another advantage is that the coating, again due to the low temperature deposition process, may be used as binder-material for biocompatible materials such as hydroxyapatites and calcium carbonates, without altering their microstructure or chemical composition, i.e. the exact biological properties is kept after deposition.

Furthermore, due to the simplicity of the method, deposition of coatings on selected sections of a substrate is possible. Also implants may be coated in a quick and simple way prior to the implant procedure.

Embodiments of the invention are defined in the dependent claims.

BRIEF DESCRIPTION OF THE DRAWINGS

The invention will be described in detail below with reference to the drawings, in which.

DETAILED DESCRIPTION OF PREFERRED EMBODIMENTS

Figure 1:
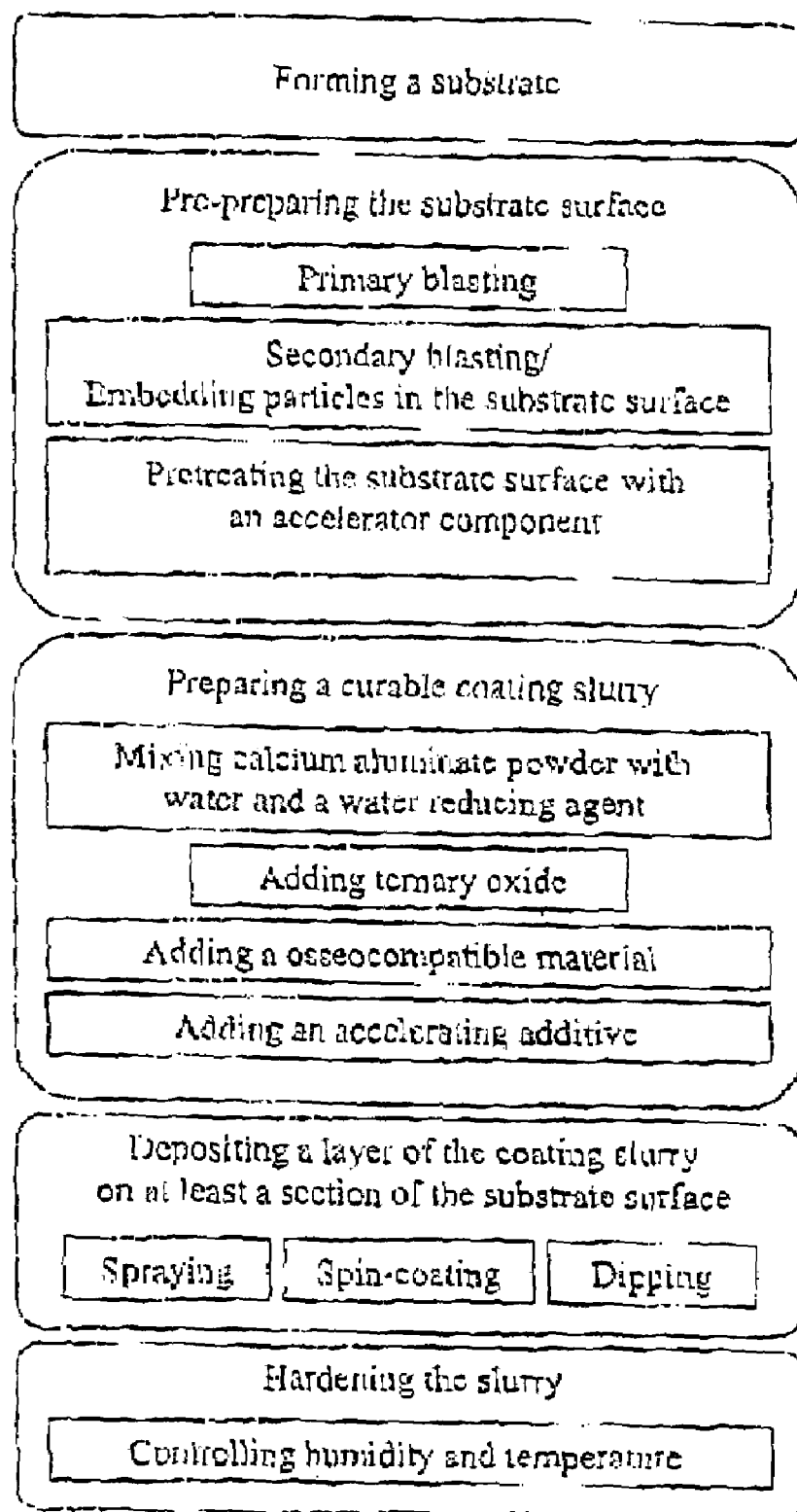
FIG. 1 shows a schematic representation of the method according to the present invention.

The present invention is mainly concerned with coatings for medical devices, e.g. implants, laboratory equipment, tools for surgery and the like. Commonly wanted bulk properties include high strength, elasticity, machinability, low leakage rates of alloy elements, etc. The requirements on the surface region include biological properties, such as toxicity, inflammation, rejection or other unwanted tissue reactions. Furthermore, the surface may exhibit different degrees of bioactivity, such as activation of cell growth, or controlled degradation, as well as being a carrier for active substances, e.g. pharmaceutical agents, growth factors, etc.

Throughout this application the term biocompatibility is used a number of times implying certain properties on the material or surface in question. However, is should be noted that biocompatibility is used as a generic term for the different properties that are required or desirable for materials that are to be in contact with biological tissue. Moreover, the material has to be used/prepared in the right way and to be used in suitable applications.

Another frequently used term is osseo-compatible, which implies that a material has especially advantageous for use in contact with bone tissue. As presented above, some osseo-compatible materials even seems to be capable of forming a direct bond with natural bone. Examples of materials considered to be osseo-compatible are hydroxyapatite, and coral-like materials of calcium carbonates.

The present invention includes a method for deposition, a coating material and products with a surface coating deposited according to the method.

The material to be coated, hereafter referred to as the substrate, may be a ceramic, metallic or polymeric material. In a preferred embodiment of the invention the substrate is a metal accepted in the field of medical implants, such as titanium, alloys of titanium, stainless steel or CoCr-alloys.

The present invention is preferably used to deposit ceramic coatings on structures or implants intended for contact with biological tissues, and especially suitable in contact with bone tissue. Examples of such structures or implants are, surface coated orthopedic implants e.g. hip- and knee joints, attachment elements (screws, nails, plates) for internal and external bone fixation and restoration of fractures.

The coating material of the invention is calcium aluminate either alone, or used as a binding phase with selected biocompatible and water reducing agent additives.

The deposition is principally performed in three steps. Firstly, the surface of the substrate is pretreated, secondly the coating is deposited as a slurry comprising calcium aluminate powder and a water soluble solvent, and thirdly the deposited slurry is hardened. The calcium aluminate-water-slurry hardens by a chemical reaction, a hydration, and is thereby bonded to the surface of the substrate. The hardening or curing of calcium aluminates is described in our co-pending Swedish patent application SE-0104441-1, "Ceramic material and process for manufacturing", filed Dec. 27, 2001.

To achieve a coating with optimal properties, the following steps are performed:

Pretreatment of the substrate surface

Preparation of the slurry, including addition of additives

Depositing the slurry on the substrate surface, and

Hardening of the slurry.

Each of these steps will now be presented more in detail (FIG. 1).

Pretreatment of the Substrate Surface

It has been shown that a substrate surface pretreated with sand blasting in two steps result in optimal bonding between the coating and the substrate surface. The first blasting step is preferably performed with hard ceramic particles, generating a surface roughness with surface roughness values, $R_a$-values, in the range of 0.1 to 10.0 µm.

Most preferably the primary blasting is performed as a wet-blasting, whereby the resulting surface has been shown to be substantially free from blasting material. This is of great importance as the substrate is to be used in biological applications.

The primary blasting may alternatively be another abrasive process producing the same surface roughness, such as grinding with hard particles or grit.

The second blasting is performed with calcium aluminate particles as blasting medium. The second blasting should preferably be performed in such a way that calcium aluminate fragments are embedded into the substrate surface. The aim of this blasting is to achieve a better anchoring of the coating on the substrate, and to provide seed points for the following hydration of the calcium aluminate. This step may be achieved with dry blasting or other impingement method that produces relatively high particle speeds.

To further enhance the bonding between the substrate and the coating, the substrate may thereafter be pretreated with a water solution containing an accelerator component that accelerates the hardening process of the calcium aluminate. Such accelerator components are well known in the field. Lithium chloride (LiCl) has been shown to be an especially suitable accelerator. The purpose of the pretreatment with salt is to initiate the hydrating process in a controlled way directly on the substrate surface, whereby porosity, cracking etc. is avoided at the coating/substrate interface.

The calcium aluminate-water-slurry may be applied to the substrate surface either before or after the pretreated substrate has dried.

Preparing the Slurry

As stated above, the slurry is comprised of a water-based solvent and a powder, mainly comprised of ceramic components.

To achieve desired hardening characteristics and suitable properties of the slurry, the water-based solvent comprises one or more additives. Preferably, the solvent is comprised of water, and one or more components with dispersing, water-reducing, and wetting improving properties (hereafter referred to as water-reducing-agents). To achieve desired hardening times, the solvent often also comprises one or more components that accelerates the hardening process (hereafter referred to as accelerator-agents).

One suitable accelerator-agent is LiCl, which is well known as accelerator-agent in the concrete industry. To achieve suitable hardening speeds, the solvent may include from 0.01% to 1.0% by weight, preferably 0.05–0.1%. By altering the content of the accelerator-agent in the solvent, the hardening speed may be adjusted to be optimal for a specific application.

Examples of other salts that may be used as accelerator- or retarding agents are: lithium hydroxide, lithium carbonate, lithium sulfate, lithium nitrate, lithium citrate, calcium hydroxide, potassium hydroxide, potassium carbonate, sodium hydroxide, sodium carbonate, sodium sulfate and sulfuric acid.

Generally, fast hardening is preferable when deposition of the slurry is performed by spraying, and slow hardening is preferable when deposition is performed by dipping or a spin coating method.

Addition of water-reducing-agents (WRA) is needed to improve the wetting properties of the slurry, whereby the adhesion to the substrate is increased. It also leads to a more homogenous hydration process, whereby cracking; porosity etc in the substrate-coating interface is avoided.

Examples of such water-reducing-agents are water solutions of polycarboxylic polymers with PEG chains, and polyacrylic acids also with attached organic chains. Specific examples of water reducing products are: Conpac 30 (Perstorp AB) Dispex A40 (Ciba GmbH, Schweiz), Glenium 151 (Master Builders, Italy) SSP20 (Cementa AB, Sweden).

To achieve the desired effects, the solvent should include from 0.05 to 5% by weight, preferably 0.1–1%. Preferably, the resulting slurry should have a water to cement ratio (w/c) in the range of 0.1 to 0.9, preferably 0.1 to 0.4, to achieve a suitable viscosity. Alternatively, the solvent may be pure water, and the additives may be added in dry state to the ceramic powder prior to the mixing with water or to direct to the slurry.

In a basic form of the present invention, the mixture of ceramic powder is only comprised of calcium aluminate. A number of stoichiometries exist for the system. Commercially available powders consist mainly of CA or $CA_2$, where C stands for CaO and A for $Al_2O_3$, according to accepted cement chemistry notations. The phases $C_{12}A_7$ and $CA_6$ and $C_3A$ have also been described in the literature. All phases are applicable on the present invention. Such powders with sufficient quality are commercially available products, e.g. Secar and Ternal White from LaFarge Aluminates.

Binding phase systems based on hydrated calcium aluminate have unique properties. In comparison to other water binding systems, for example silicates, carbonates and sulphates of calcium, the aluminates are characterised by high chemical resistance, high strength and a relatively rapid curing.

The high strength of calcium aluminate cements is due to the high absorption capacity of hydrated water, which in turn results in a low residual water contents and low porosity. The high compaction also increases the resistance to corrosion.

Generally, if a calcium aluminate powder is mixed with a water-based solution, a hardening process is initiated through a chemical reaction between the calcium aluminate particles and water. More precisely, this hardening process is a hydration, whereby a new binder phase comprised of calcium aluminate hydrate is formed. The hydrates are formed by nucleation of crystalline hydrate phase from the liquid phase. The hydrate is thereafter transformed into different crystalline phases, with a rate depending on e.g. temperature and additives. At room temperature the initially formed hydrate phase is $CAH_{10}$, where $H=H_2O$, and the most stable phase is $C_3AH_6$.

As disclosed in our co-pending Swedish patent application, SE-0104441-1, the coating may further comprise a material, e.g. for reducing the aluminum content in coating. As is proposed in SE-0104441-1 calcium titanates, $Ca/TiO_3$, or other variants where Ti may be substituted by Zr or Hf and Ca by Mg, Ca, Sr or Ba, in a perovskitic structure, are preferred for this purpose, because they are biologically suitable and they do not substantially affect the mechanical properties of the material. I fact, all material compositions disclosed in SE-0104441-1 are applicable as coating materials in the present invention.

When needed, the ceramic powder is treated by a suitable milling process to obtain a uniform and well controlled size distribution. One such type of milling process is presented in the example below, but other milling processes known in the field of ceramics could be used as long as the desired result is reached.

More in general, the method according to the present invention may be used to produce coatings of any material with a binder-phase of hydrated calcium aluminate, which may be applied to a substrate in the form of a slurry where after it hardens.

Depositing the Slurry on the Substrate

The slurry may be applied onto the substrate in a large number of ways, such as spray deposition, brush painting, spin-coating, dipping and the like.

To achieve a coating with optimal properties, in terms of strength, ductility etc, the coating should have a thickness in the order of 0.1–200 µm, preferably less than 30 µm. Optimal properties are related to the possibility to produce an essentially defect-free coating. As the size of defects normally is in the order of one to a few µm, there is no space available for defects in sufficiently thin coatings, and the strength of the coating may approach the theoretical limit for the material, which normally is about 100 times higher compared with the bulk strength of the material.

To prevent the slurry from curing excessively fast during the deposition, the slurry may be kept at a low temperature, e.g. in the range 2 to 10° C., where after the temperature is raised to appropriate temperatures during hardening as described in detail below.

Hardening of the Slurry

To achieve a coating with optimal mechanical properties, the hardening of the applied slurry has to be performed under specific conditions. As the hydration process consumes water, it is of great importance that the applied slurry is prevented from drying, i.e. the hardening has to be performed in wet (or at least moist) conditions. Therefore the hardening is preferably performed under controlled conditions with humidity of at least 90%, e.g. saturated or oversaturated vapor, or immersed in water.

Due to the very low thickness of the deposited layer of slurry, precautions have to be taken to prevent the slurry from falling of the substrate during hardening.

The hardening of the material may be performed in the temperature range from approximately 10° C. to 100° C. Above 100° C. the water needed for the hydration is evaporated and the slurry will dry. Preferably, the hardening is performed in the range from 20° C. to 70° C. If shorter hardening times and more complete hydration are desired, the more elevated temperatures may be used. The preferable hardening conditions, in terms of temperature and humidity, may be achieved by auto-clavation.

ALTERNATIVE EMBODIMENTS OF THE INVENTION

In one embodiment, the calcium aluminate coating is used as binder phase (carrier) for other biocompatible and/or osseo-compatible materials, whereby unique combinatory properties can be achieved. comprises adding particles or powder of one or more biocompatible materials. Suitable biocompatible materials comprises different types of calcium carbonates, calcium phosphates (preferably calcium salts of ortophosphoric acid) and apatites.

Addition of fragments or particles of apatites, such as hydroxyapatite or fluorapatite or carbonates-apatites, is especially preferred. Due to the low temperatures involved in the deposition process, these materials, being extremely temperature-sensitive, can be carried by the calcium aluminate coating, and their phase composition be preserved.

Preferably, a powder of biocompatible materials is added to the ceramic powder mixture when preparing the slurry, whereafter the coating is applied onto the substrate and hardened as described above.

Such a calcium aluminate coating with improved biocompability may provide implants with osseo-compatible properties in applications where coatings of pure hydroxyapatite or the like are too weak.

The characteristics of the process and the coating material make it possible to deposit coatings on devices that are sensitive to high temperatures due to a low melting point, temperature expansion, hardening procedures and the like.

EXAMPLE

This non-limiting example describes one embodiment of the surface coating method according to the invention more in detail, and the mechanical properties of these coatings.

Figure 2:
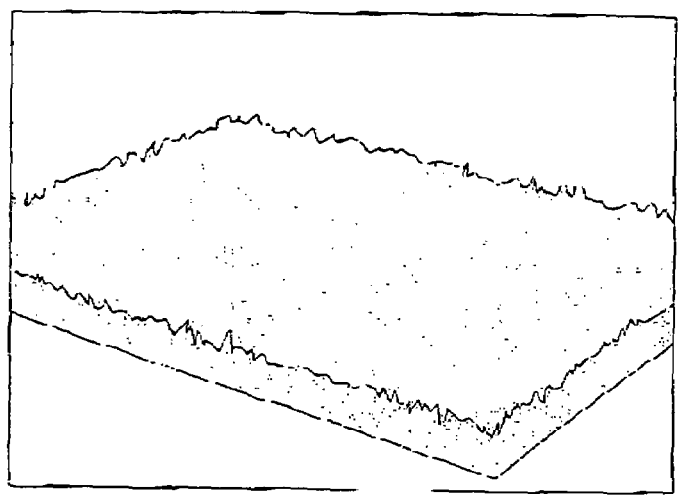
FIG. 2 shows a picture from optical profilometry (OP) measurement of a substrate surface after pretreatment step of blasting.

In this example, round bars of pure medical grade titanium, ASTM Gr.2, with a diameter of 6 mm, were used substrates. The titanium bars was pretreated with wet blasting using aluminum oxide grit with a particle size of 100–120 mesh. The blasting was performed with a pressure of 1 bar (air pressure). After blasting, the surface roughness and morphology was characterized using Scanning Electron Microscopy (SEM) and optical profilometry (OP). The surface roughness was shown to be in the range of $R_a$=0.6–0.7 µm after wet blasting, see FIG. 2.

To improve the bonding between the titanium and the coating, a secondary blasting of the metal surfaces was performed using calcium aluminate (CA) particles with a grit size between 0 and 22 µm (90%) at a pressure of ~10 bar (air pressure). The resulting surface morphology was shown by a SEM picture, where the dark areas represented CA enriched areas on the titanium surface, whereas the light areas represented areas with a smaller amount or none CA. This phenomenon is due to the lower atomic number for CA compared to titanium and was confirmed by elemental analysis using Energy Dispersive Spectroscopy (EDS) of the dark and light areas, respectively, of the CA blasted surface, CA-particles are baked into the surface.

The CA-powder for the coatings, which in this example was commercially available Ternal White, was treated by milling to obtain a uniform and well controlled size distribution. The powder was milled in iso-propanol with chemically inert silicon nitride milling balls for three days. This resulted in a powder with 99.6% of the grains having a diameter of less than 23 µm and most of the particles having a diameter of approximately 8 µm.

After milling, the milling balls were removed, and the iso-propanol evaporated. Thereafter, residual water and organic contaminations were removed by burning of the dry powder for four hours at 400° C.

The milled CA-powder was mixed with water, containing 0.01 gr of LiCl in 100 gr of water. To improve the strength of the coatings, to facilitate the spraying process, and to improve the wetting properties of the slurry, a water-reducing-agent (Conpac 30 from Perstorp AB), was added to the mixture resulting in a water to cement ratio of approximately 0.3. The slurry was mixed with a high speed rotating dispersion mixer.

The CA slurry described above was sprayed on the pre-treated titanium metal substrates to a thickness of approximately 10–30 µm, and then cured in saturated water vapor at 37° C. for 72 hours.

The adhesion strength between coating and titanium surface was tested with a torsion strength tester. All samples were prepared by casting the sprayed titanium bars in a mould inside the test equipment. The test equipment is based on a collet clamped in a chuck, connected to a lever arm. The lever arm is in contact with a pushing rod, a strain gauge sensor and a position indicator.

The adhesion test was performed by slowly bringing the lever arm forward with the aid of the piston. The position of the piston and the force of the lever on the piston were recorded, giving a measure of the force and deformation distance required to wrench loose the round bar.

Figure 3:
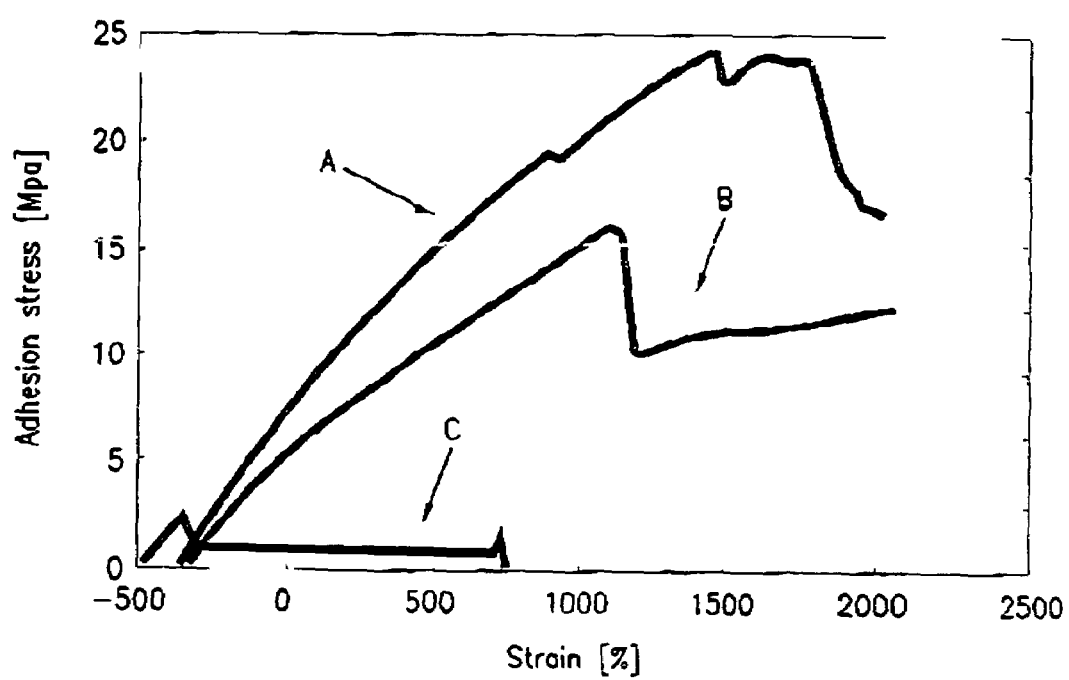
FIG. 3 is a diagram comparing the coating adhesion for pins pretreated in three different ways.

FIG. 3 compares the coating adhesion for pins pretreated in three different ways: grinding with silicon carbide C, silicon carbide dry blasting B, and wet alumina blasting followed by CA blasting A.

Figure 4:
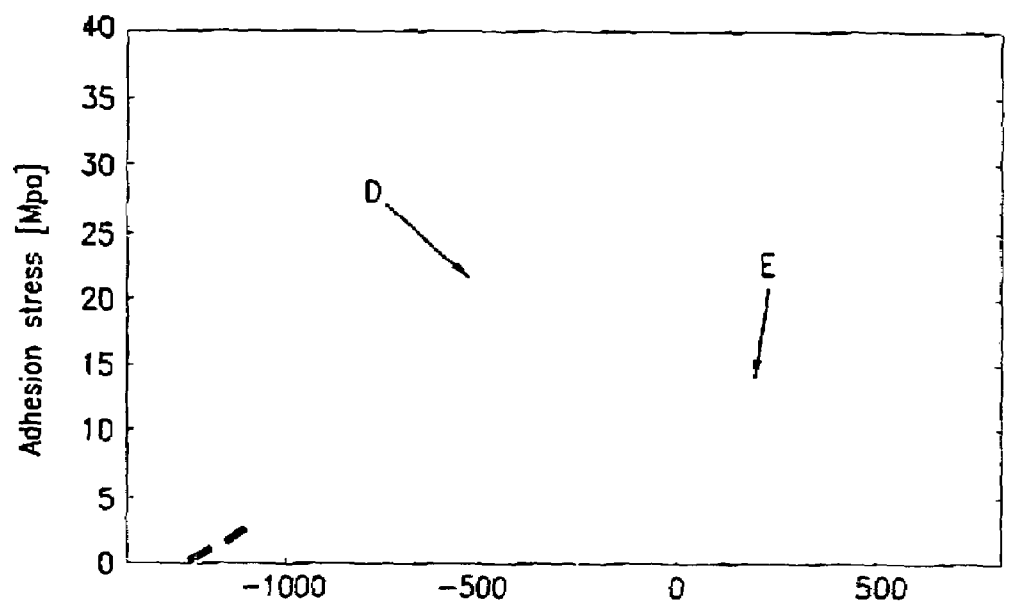
FIG. 4 is a diagram comparing the coating adhesion of the CA coating prepared from a slurry comprising a water-reducing-agent with a coating prepared from a slurry not comprising a water-reducing-agent.

In FIG. 4 the adhesion of the CA coating to the metal substrate is demonstrated for a coating prepared from a slurry comprising a water-reducing-agent D and for a coating prepared from a slurry not comprising a water-reducing-agent E.

Figure 5:
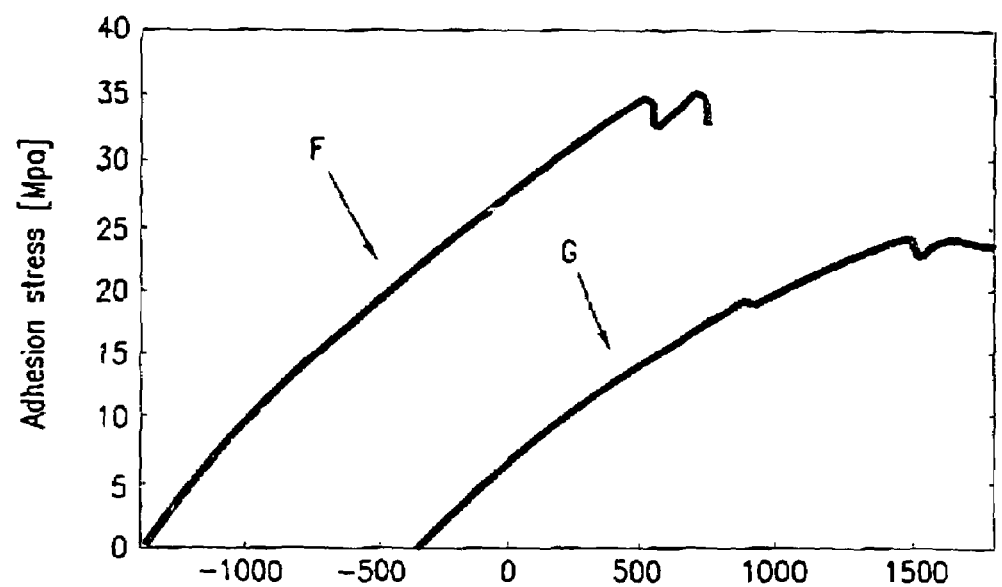
FIG. 5 is a diagram comparing the adhesion between coating and titanium metal pretreated by wet alumina blasting and wet alumina blasting followed by CA blasting.
Figure 4:
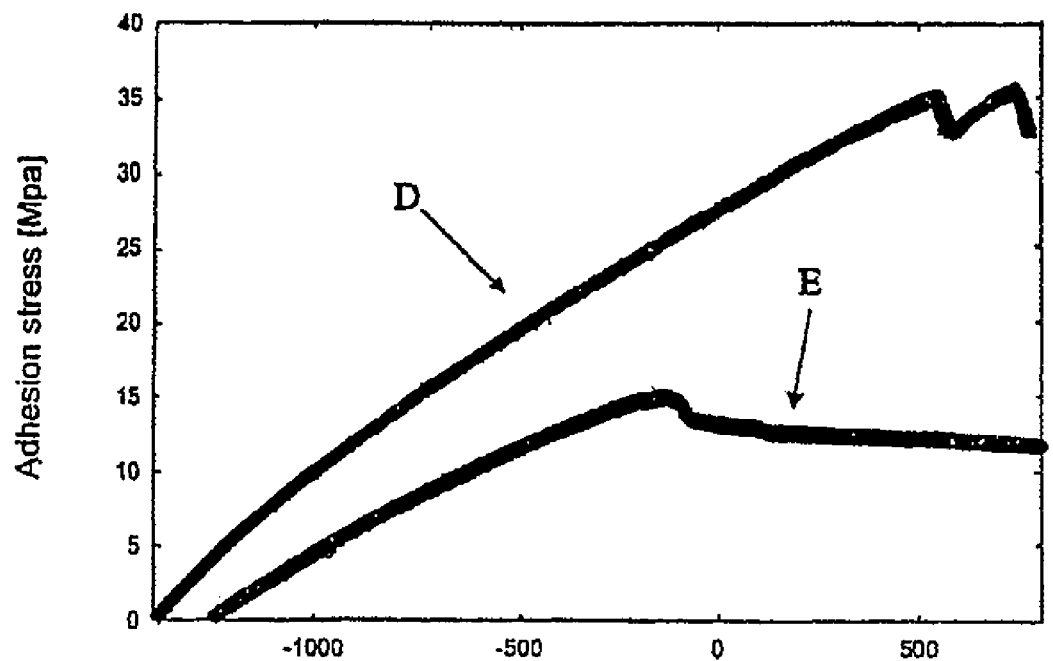
Figure 5:
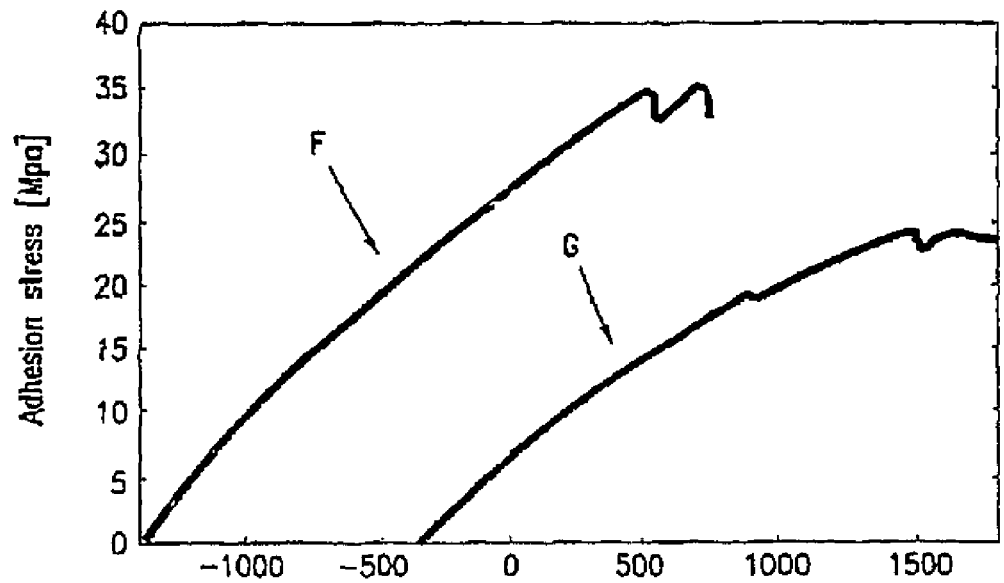

FIG. 5 compares the adhesion between coating and titanium metal pretreated by wet alumina blasting G and wet alumina blasting followed by CA blasting F.

To conclude, it is obvious from the example that the different techniques for pretreating the substrate surface, as well as the addition of the water-reducing-agent, play a central role when a strong adhesion between the coating and the substrate surface is desired. With suitably selected pretreatments and additives, adhesion values comparable to the bulk strength of the cement are achieved.

The invention claimed is:

1. Surface coating method for deposition of a chemically bonded ceramic coating on a substrate, comprising the steps of:
    preparing a curable coating slurry, comprising mixing calcium aluminate powder with water and at least one water-reducing-agent, such that a water-to-cement ratio in the range of 0.1 to 0.9 is achieved;

depositing a coating of the slurry on at least a section of the substrate surface, and hardening the slurry.

2. Surface coating method according to claim 1, wherein the step of preparing a curable coating slurry comprises adding a ternary oxide of perovskite structure according to the formula $ABO_3$, where O is oxygen and A and B are metals, or any mixture of such ternary oxides.

3. Surface coating method according to claim 2, wherein the ternary oxide is calcium titanate.

4. Surface coating method according to claim 1, wherein the step of preparing a curable coating slurry comprises adding particles or powder of one or more biocompatible materials.

5. Surface coating method according to claim 4, wherein the biocompatible material is a calcium carbonate.

6. Surface coating method according to claim 4, wherein the biocompatible material is a calcium phosphate.

7. Surface coating method according to claim 4, wherein the biocompatible material is an apatite.

8. Surface coating method according to claim 7, wherein the apatite is selected from the group comprised of fluorapatite or carbonates-apatites.

9. Surface coating method according to claim 7, wherein the apatite is hydroxyapatite.

10. Surface coating method according to claim 4, wherein the biocompatible material is a calcium salt with orthophosphoric acid.

11. Surface coating method according to claim 1, wherein the step of preparing a curable coating slurry comprises addition of a component which accelerates or retards the hardening process.

12. Surface coating method according to claim 1, further comprising the step of: pre-treating the substrate surface to a surface roughness in the range of Ra 0.1 to 10.0 µm before deposition of the slurry.

13. Surface coating method according to claim 12, wherein the pretreatment is performed by dry blasting with hard particles.

14. Surface coating method according to claim 12, wherein the pretreatment is performed by wet-blasting with hard particles.

15. Surface coating method according to claim 1, further comprising the step of: embedding calcium aluminate fragments in the substrate surface.

16. Surface coating method according to claim 15, wherein the embedding is performed by blasting the surface with calcium aluminate fragments or powder.

17. Surface coating method according to claim 1, further comprising the step of: pre-treating the substrate surface with an accelerator-agent for accelerating the hardening process.

18. Surface coating method according to claim 1, wherein the step of applying the slurry is performed by spraying, spin coating or dipping.

19. Surface coating method according to claim 1, wherein the step of hardening is performed in water or in a environment with at least 90% relative humidity.

20. Surface coating method according to claim 1, wherein the step of hardening comprises controlling the temperature to be in the range of 10° C. to 200° C., preferably in the range 20° C. to 70° C.

21. Surface coating method according to claim 1, wherein the deposited coating has a thickness in the order of 0.1–200 µm.

22. Method of producing a surface coated biocompatible device, comprising the steps of:

forming a substrate depositing a biocompatible surface coating covering at least a section of the substrate surface using the surface coating method according to claim 1.

* * * * *

UNITED STATES PATENT AND TRADEMARK OFFICE
CERTIFICATE OF CORRECTION

PATENT NO. : 7,074,223 B2
APPLICATION NO. : 10/322569
DATED : July 11, 2006
INVENTOR(S) : Niklas Axen et al.

It is certified that error appears in the above-identified patent and that said Letters Patent is hereby corrected as shown below:

Please replace Figure 4 with the accompanying Figure 4. (as shown on the attached page)

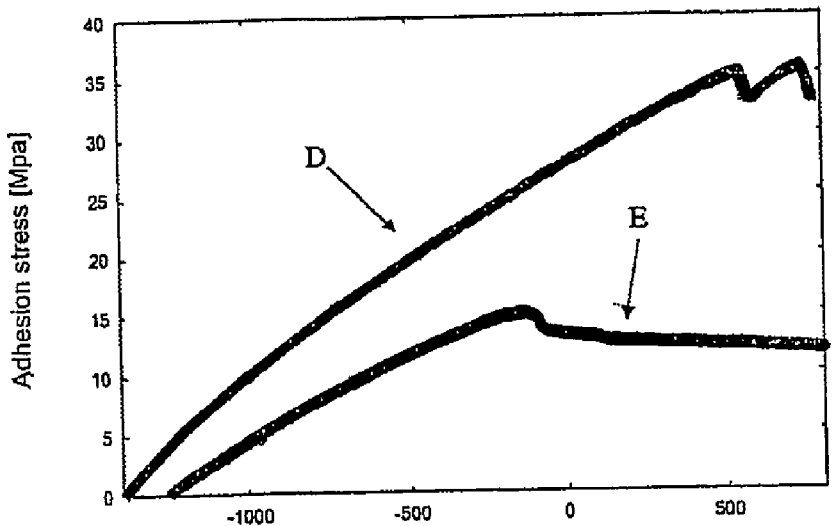

Fig. 4

Signed and Sealed this

Ninth Day of January, 2007

JON W. DUDAS
*Director of the United States Patent and Trademark Office*